US010988663B2

(12) United States Patent
Goodman et al.

(10) Patent No.: US 10,988,663 B2
(45) Date of Patent: Apr. 27, 2021

(54) METHOD FOR SEALING A VOID IN A WELL USING A SMART GEL SEALANT

(71) Applicants: Chevron U.S.A. Inc., San Ramon, CA (US); Los Alamos National Laboratory, LC / IP, Los Alamos, NM (US)

(72) Inventors: Harvey E. Goodman, Houston, TX (US); Robert Clifford Roback, Los Alamos, NM (US); Robert D. Gilbertson, Los Alamos, NM (US); Hakim Boukhalfa, Santa Fe, NM (US); Scott W. Imbus, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 190 days.

(21) Appl. No.: 16/091,943

(22) PCT Filed: Apr. 4, 2017

(86) PCT No.: PCT/US2017/025827
§ 371 (c)(1),
(2) Date: Oct. 5, 2018

(87) PCT Pub. No.: WO2017/176664
PCT Pub. Date: Oct. 12, 2017

(65) Prior Publication Data
US 2019/0292435 A1    Sep. 26, 2019

Related U.S. Application Data

(60) Provisional application No. 62/319,630, filed on Apr. 7, 2016.

(51) Int. Cl.
*E21B 47/10*   (2012.01)
*C09K 8/508*   (2006.01)
(Continued)

(52) U.S. Cl.
CPC ............ *C09K 8/5083* (2013.01); *A61P 31/18* (2018.01); *C07D 401/14* (2013.01);
(Continued)

(58) Field of Classification Search
CPC ...... C09K 8/5083; C09K 8/508; C09K 8/512; E21B 33/13; E21B 47/10
See application file for complete search history.

(56) References Cited

U.S. PATENT DOCUMENTS 3,749,172 A * 7/1973 Hessert ................. C09K 8/887
166/400
4,569,393 A * 2/1986 Bruning ................. C09K 8/512
166/270

(Continued)

FOREIGN PATENT DOCUMENTS

EP    1331262 A1    7/2003
EP    1384771 A1    1/2004
(Continued)

OTHER PUBLICATIONS

International Search Report issued in PCT/US2017/025827, dated Jun. 1, 2017, 3 pages, European Patent Office.

*Primary Examiner* — Silvana C Runyan
(74) *Attorney, Agent, or Firm* — King & Spalding LLP

(57) ABSTRACT

Embodiments of the disclosure include swellable smart gel sealants. In certain embodiments, the smart gel sealants reversibly swell when exposed to a certain trigger, such as temperature or pH. In specific embodiments, the smart gel is disposed within voids in a well and triggered to swell in order to seal the voids. One application of the smart gel sealant is to seal the casing of a well against the leakage of gas, such as $CO_2$.

24 Claims, 4 Drawing Sheets

(51) Int. Cl.
*C09K 8/512* (2006.01)
*E21B 33/13* (2006.01)
*C07D 401/14* (2006.01)
*C07D 403/12* (2006.01)
*C07D 403/14* (2006.01)
*C07D 413/14* (2006.01)
*A61P 31/18* (2006.01)

(52) U.S. Cl.
CPC ......... *C07D 403/12* (2013.01); *C07D 403/14* (2013.01); *C07D 413/14* (2013.01); *C09K 8/508* (2013.01); *C09K 8/512* (2013.01); *E21B 33/13* (2013.01); *E21B 47/10* (2013.01)

(56) References Cited

U.S. PATENT DOCUMENTS

| | | | |
|---|---|---|---|
| 5,888,943 A | 3/1999 | Diggs et al. | |
| 2010/0065273 A1* | 3/2010 | Sawdon | C09K 8/24 166/293 |
| 2011/0187556 A1* | 8/2011 | Roddy | G01V 3/00 340/853.3 |
| 2013/0000900 A1 | 1/2013 | Kalgaonkar et al. | |
| 2017/0138149 A1* | 5/2017 | Muthusamy | E21B 33/1208 |
| 2018/0037798 A1* | 2/2018 | Mishra | C04B 28/02 |

FOREIGN PATENT DOCUMENTS

| | | |
|---|---|---|
| GB | 2524232 A | 9/2015 |
| WO | WO 2015/126402 A1 | 8/2015 |

\* cited by examiner

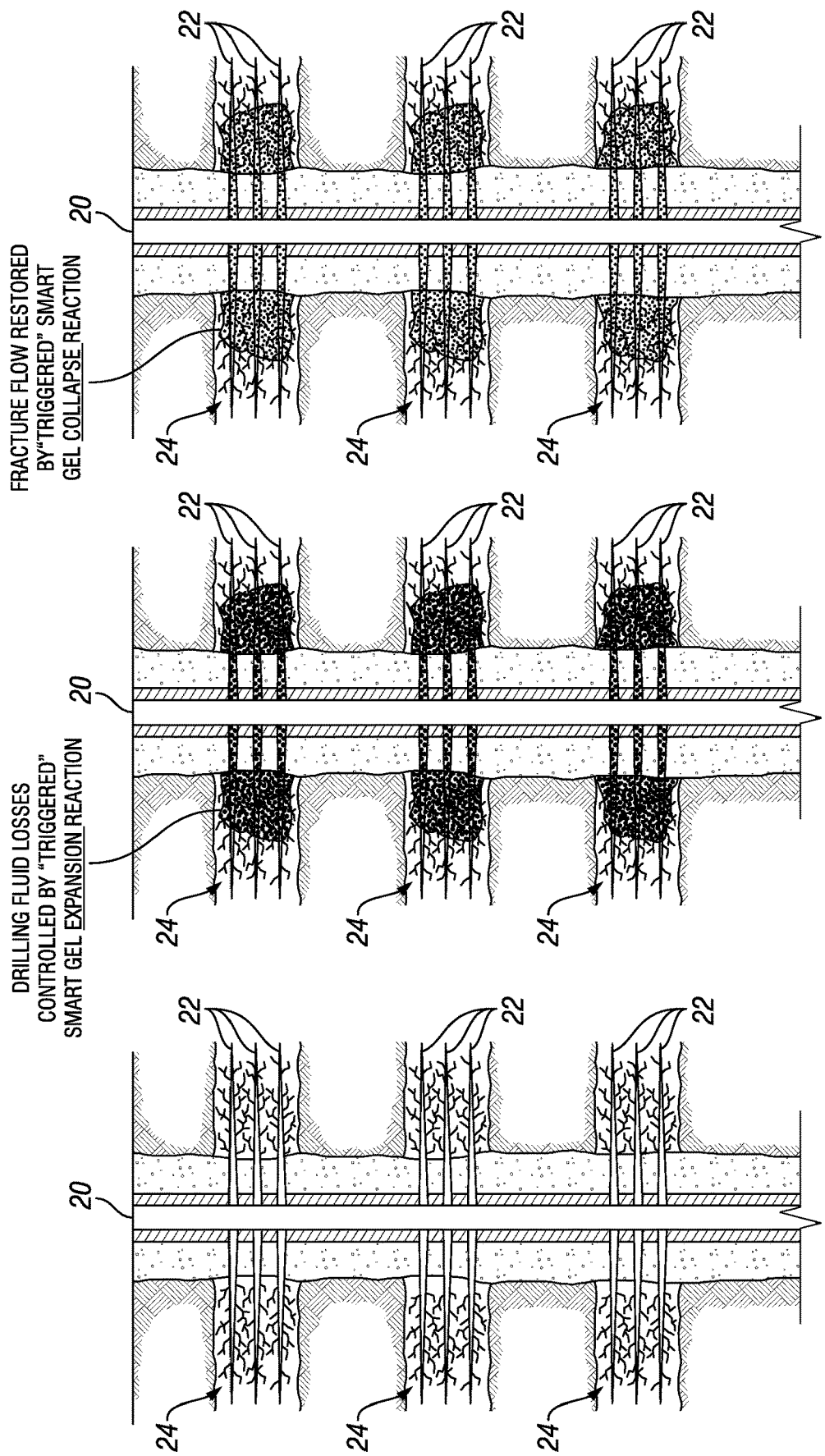

METHOD FOR SEALING A VOID IN A WELL USING A SMART GEL SEALANT

CROSS-REFERENCE TO RELATED APPLICATIONS

The present application is a national phase application of and claims priority to PCT/US2017/25827 filed on Apr. 4, 2017, which claims the benefit of U.S. Provisional Patent Application No. 62/319,630, filed on Apr. 7, 2016, the forgoing applications are herein incorporated by reference in full.

ACKNOWLEDGEMENT OF GOVERNMENT SUPPORT

The claimed invention was made with government support under Contract No. DE-AC52-06NA25396 awarded by the U.S. Department of Energy. The government has certain rights in the claimed invention.

PARTIES TO JOINT RESEARCH AGREEMENT

The research work described here was performed under a Cooperative Research and Development Agreement (CRADA) between Los Alamos National Laboratory (LANL) and Chevron under the LANL-Chevron Alliance, CRADA number LA05C10518.

TECHNICAL FIELD

The present disclosure relates generally to methods to use triggerable swellable gel sealants, and more specifically to methods to use triggerable, swellable, gel sealants to enhance, maintain, or repair subsurface integrity within wells.

BACKGROUND

The safe, environmentally friendly, and cost efficient exploitation of oil and gas resources is becoming increasingly complex. For example, deep water subsalt developments require fewer wells that must produce reliably over longer periods of time to justify the large capital expenditures necessary to develop them. Enabling technologies being developed focus on a wide range of applications along the entire value chain used to discover, recover and transport high energy density resources to the consumer. Given the additional time a well is required to produce, additional complexities are added to maintaining the safe and cost effective maintenance of the well.

New compositions, methods, and systems are needed to enhance, maintain, or repair subsurface integrity within near well bore regions. For example, oil and gas producing wells typically experience high pressure conditions, which could lead to pressure containment losses, for instance, $CO_2$ leakage through microannuli (e.g. delaminations along the interface of steel and cement) in the well system.

SUMMARY

A general embodiment of the disclosure is a method of mitigating gas leaks in a well-head, comprising: monitoring a well-head for a gas leak; upon detecting the gas leak, injecting into the well-head a triggerable gel composition comprising a swellable polymer where the polymer backbone comprises an inert monomer, a practical monomer, and less than 1.5% by weight of a cross-linker, wherein when the triggerable gel composition is exposed to a trigger, the triggerable gel composition swells to at least ten times the size of the original polymer. The general embodiment can further comprise injecting a second composition into the well-head that will trigger the gel composition to swell. The trigger can be pH, temperature, ion concentration, magnetic waves, acoustic waves, electric waves or $CO_2$, for example. In specific embodiments, the trigger is $CO_2$ and the $CO_2$ could be present prior to injecting the triggerable gel composition into the well, or alternatively, the trigger could be emplaced into the well in anticipation of $CO_2$ eventually being sourced into the well. In embodiments the inert monomer is one or more of methyl methacrylate, styrene, alkyl substituted styrenes, methyl acrylate, methacrylic and acrylic monomers, acryloyl nitrile, polyvinylpyrolidinone and a substituted acrylamide and/or the inert monomer is 5-80% by weight of the triggerable gel. In embodiments, the practical monomer is one or more of 2-(dimethylamino) ethyl methacrylate, vinyl pyridine, 2-(diethylamino) ethyl acrylate, 3-(dimethylamino)propyl acrylate, and acrylic acid and/or the practical monomer is 5-80% by weight of the triggerable gel. In embodiments, the cross-linker is one or more of ethylene glycol dimethacrylate, methylene bis-acrylamide, triethyleneglycol trimethacyrlate, and divinyl- or trivinyl benzene. Additionally, the triggerable gel composition can be comprised within a working fluid such as water, brine, or a drilling fluid. In specific embodiments, the average size of the gel particles is between 10 nanometers to 100 micrometers. The polymer may comprise less than 1% of cross-linker.

Another general embodiment of the disclosure is a method for sealing voids in a well comprising: injecting into the well a triggerable gel composition comprising an inert monomer, a practical monomer, less than 1% by weight of the polymer of a cross-linker, wherein when the triggerable gel composition is exposed to a trigger, the triggerable gel swells to at least ten times the size of the gel composition when originally injected. In specific embodiments, the void being sealed is a void in a sand screen, microannulus in a casing of the well, or voids in a production zone of a well undergoing drilling. Additionally, the general embodiment can further comprise injecting a second composition into the well that will trigger the gel composition to swell, such as a composition that changes the pH, temperature, ion concentration, magnetic waves, acoustic waves, electric waves or $CO_2$ of the area around the void that comprises the triggerable gel composition. In specific embodiments, the trigger is $CO_2$ and the $CO_2$ is present in the well prior to injection of the gel into the well. For example, the $CO_2$ could be native to the well or sourced into the well prior to or after injection. In specific embodiments, the inert monomer is one or more of methyl methacrylate, styrene, alkyl substituted styrenes, methyl acrylate, methacrylic and acrylic monomers, acryloyl nitrile, polyvinylpyrolidinone and a substituted acrylamide and/or the inert monomer is 5-80% by weight of the triggerable gel. In embodiments, the practical monomer is one or more of 2-(dimethylamino) ethyl methacrylate, vinyl pyridine, 2-(diethylamino) ethyl acrylate, 3-(dimethylamino)propyl acrylate, and acrylic acid and/or the practical monomer is 5-80% by weight of the triggerable gel. In embodiments, the cross-linker is one or more of ethylene glycol dimethacrylate, methylene bis-acrylamide, triethyleneglycol trimethacyrlate, and divinyl- or trivinyl benzene. Additionally, the triggerable gel composition can be comprised within a working fluid such as water, brine or a drilling fluid. The void being sealed may also be in a near wellbore region such as within 20 meters of the wellbore, within 10 meters of the wellbore, within 8 meters of the wellbore, within 5 meters of the wellbore, within 3 meters of the wellbore, within 2 meters of the wellbore, within 1 meter of the wellbore, or within 0.5 meters of the wellbore. Additionally, the average size of the gel particles can be between 10 nanometers and 100 micrometers.

These and other aspects, objects, features, and embodiments will be apparent from the following description and the appended claims.

BRIEF DESCRIPTION OF THE DRAWINGS

The drawings illustrate only example embodiments of methods for using triggerable, swellable, gel sealants and are therefore not to be considered limiting of its scope, as triggerable, swellable gel sealants may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

FIG. 2 illustrates the use of smart gels in drilling induced fracturing.

DETAILED DESCRIPTION OF EXAMPLE EMBODIMENTS

The example embodiments discussed herein are directed to methods of using triggerable swellable gel sealants. While the examples shown in the figures and described herein are directed to use in a wellbore, examples of triggerable swellable gel sealants can also be used in other applications in a wellbore. Thus, the examples of triggerable, swellable, smart gel sealants described herein are not limited to use in the casing and cement sheath. For example, the reversible triggerable smart gels described here may also be used in other applications such in plugging voids in sand screens, and reversibly plugging near wellbore production zone voids during drilling, completion, production, and plugging of wells. Specific embodiments of the disclosure provide means to reversibly seal cased and cemented well systems that have lost containment.

"Smart gels" or "triggerable gels," as used herein, refer to a class of polymer gels that swell upon sensing a specific trigger. The smart gel may also collapse when the trigger is removed. Triggers include, but are not limited to, pH, temperature, concentration of metal ions, and/or acoustic, electric, and/or magnetic stimuli. The swellable element within the smart gel swells to at least ten times the original size of the smart gel (size prior to trigger) when the trigger is applied.

As used herein, numerical values recited refer to values equal to the numerical value or values within the standard of error of measuring such values. The term "about," as used herein, refers to an amount that is within 3% of the value recited.

The term "inert monomer," as used herein, refers to a monomer within a smart gel polymer that does not respond to a triggering event.

The term "practical monomer," as used herein, refers to a monomer within a smart gel polymer that undergoes a physical and/or chemical transformation when exposed to a trigger.

The term "cross-linker," as used herein, refers to a di- or tri- or otherwise multi-functional monomer that causes cross-linkages to occur within the smart gel polymer.

The term "microannulus" or "microannuli" refers to annulus of less than 120 microns.

The term "void" as used herein is a section of a well that does not contain a solid, for example, only gas and/or liquid. For example a void could be a microannulus or a fracture, a fracture network or a gap in a sand pack.

Figure 1:
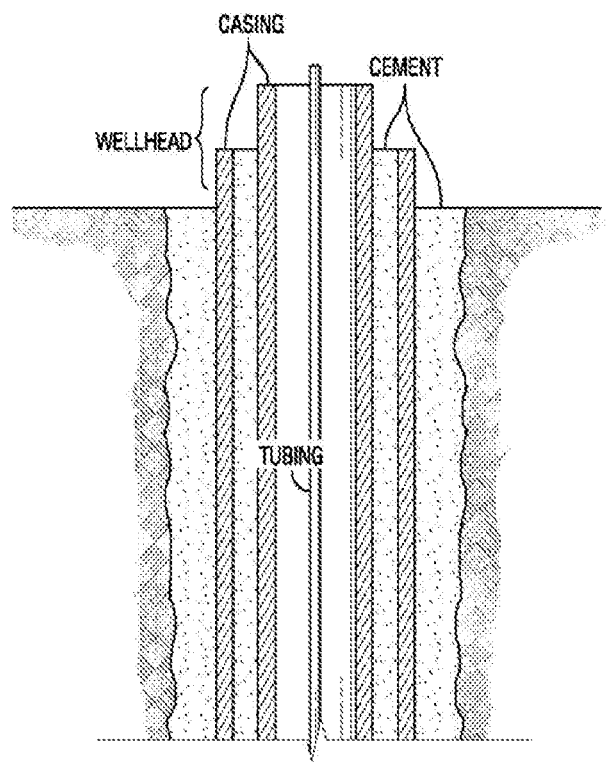
FIG. 1 is diagram of a well including the wellhead.

Embodiments of the disclosure include a polymer comprising gel particles, referred to herein as "smart gels" or "triggerable gels," that are engineered to expand or collapse when triggered by an external stimulus. In embodiments, the smart gel particles are engineered to a designed particular size range so that they can be pumped as a suspension in an appropriate working fluid into voids, such as a microannulus in a cemented wellbore. FIG. 1 illustrates one embodiment of a well system. Voids can occur throughout the well system, for example within the wellhead, the cement, the tubing and the casing. The smart gel is emplaced into the voids in a collapsed state, where it remains until it is triggered to cause expansion, filling the voids. In embodiments, the gel expansion creates a reversible localized seal that reduces or eliminates liquid and gas flow within the targeted void. If desired, the flow within the void can be restored by collapsing the smart gel by reversing the trigger. Embodiments of this disclosure relate to the use of swellable triggerable gel sealants to mitigate gas leakage from well casings.

In embodiments of the disclosure, once the gel is triggered it swells to seal void areas. The triggering event may also crosslink the practical monomers within the gel. In embodiments of the disclosure, the packing of the swollen particles and the cross-linkage strength of the individual swollen particles should be able to withstand the pressure from the formation and any fluids or gasses entering or exiting the sealed area. In some embodiments, exposure to the trigger can result in swelling ratios that may vary from a factor of 10 up to a factor of 100, such as from 10-60, 31-60, 10-20, 21-40, 41-60, 11-20, 21-30, 31-40, 41-50, 51-60, 61-70, 71-80, 81-90, and 91-100 times the unswollen smart gel particle size. In embodiments of the disclosure, the amount of swelling of the smart gels is controllable via their polymer chemistry and may be adjusted for specific applications.

In embodiments of the disclosure, the gels can be designed to be triggered by pH, $CO_2$, temperature, ionic strength, or concentration of metal ions such as calcium, acoustic waves, magnetic, heat, pressure change, or electric fields, for example. Triggering fluids or gasses could be injected, or physical changes could also be induced by specific instruments. In a specific embodiment, the gels are triggered to expand by a low pH trigger. The polymers may be designed so that the functional groups within the polymer (example: tertiary amines) react with the bicarbonate anions to form a complex through hydrogen bonding NH+ . . . —O$_3$CH which crosslinks the polymer and increases its viscosity. This process can be reversed by disrupting the hydrogen bond network by increasing the pH, which causes the deprotonation of the bicarbonate anion and the tertiary amine groups, for example. Smart gels may also be engineered such that they can be triggered by other stimuli including brine concentration, acoustics, specific ion recognition, and thermal changes. One or more of these stimuli may be preferential in a given situation. For example, the smart gel can be formulated to be in solution in a base composition at a higher pH than 7. Dropping below a pH of 6.3 could then trigger the swelling and/or crosslinking of the polymer within the smart gel. In additional embodiments of the disclosure, the trigger is reversible. For example, if the pH is again raised to be higher than 7 the smart gel shrinks to smaller than its swollen size. The smart gel can then be removed from the voids or left in place.

In embodiments of the disclosure, the polymer smart gels comprise a mixture of hydrophobic monomers as well as co-monomers that are equipped with functional groups that can be triggered to initiate cross linking or swelling in the smart gel. The practical monomer, inert monomer, and the crosslinker are all polymerized prior to injection. In some embodiments, smart gels may be colloidal particles that are hydrophobic in nature. In some specific embodiments, when exposed to a trigger, such as low pH, the amine group in colloidal hydrophobic particles becomes charged, which, in turn, can make the particles hydrophilic in nature. The smart gels can be synthesized by emulsion polymerization, which generates spherical particles. Examples of smart gels for use in embodiments are polymer microspheres with a random copolymer backbone comprising one co-monomer which is inert with respect to the triggering stimulus (herein referred to as an "inert monomer") and another co-monomer that undergoes a chemical or physical change in response to the stimulus (herein referred to as a "practical monomer"), which initiates swelling of the smart gel. In some embodiments, a fluorescent tag or non-fluorescent dyes are added to the gel in order to visualize the smart gel during experiments. The inert monomer and the practical monomer can be added to the smart gel in ratios of about 2:1-1:2, for example about 1:2, 1.1:1, 1.2:1, 1.3:1, 1.4:1, 1.5:1, 1.6:1, 1.7:1, 1.8:1, 1.9:1, 2:1, 1:1.1, 1:1.2, 1:1.3, 1:1.4, 1:1.5, 1:1.6, 1:1.7, 1:1.8, 1:1.9. The ratios of inert to practical monomers can affect how much the smart gel swells when triggered. For example, the higher the ratio of inert monomer to practical monomer, the less the smart gel swells. The higher the ratio of practical monomer to inert monomer, the more the smart gel swells. Further, increasing the concentration of cross-linker will lead to less swelling. In this way the smart gel can be tailored to specific applications. A specific smart gel embodiment is given below in Table 1. In this embodiment the smart gel comprises methyl methacrylate as the inert monomer, 2-(dimethylamino) ethyl methacrylate as the practical monomer, 2-naphtyl methacrylate as a fluorescent tag, and ethylene glycol dimethacrylate as the cross-linker.

TABLE 1

Example components of a smart gel

| Monomer | Role in Smart Gel Particle | Chemical Structure |
|---|---|---|
| Methyl methacrylate | Primary constituent of polymer chains (inert) | 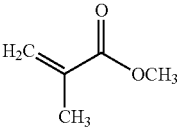 |
| 2-(Dimethylamino) ethyl methacrylate | pH-sensitive constituent of polymer chains (practical) | 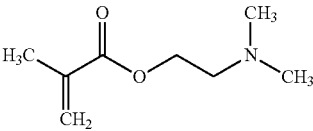 |
| 2-Naphtyl methacrylate | Fluorescent tag for experimental visualization | 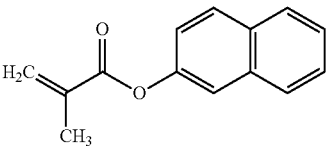 |
| Ethylene glycol dimethacrylate | Cross-linker | 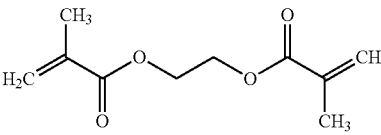 |

Examples of monomers that are inert with respect to the triggering event are styrene, alkyl substituted styrenes, methyl methacrylate, methyl acrylate or other similar methacrylic and acrylic monomers, acryloyl nitrile, PVP (polyvinylpyrolidinone) and/or other substituted acrylamides. Inert monomers can be included in the polymer of the smart gel at concentrations of 5-80% of the polymer. For example, the inert monomer can be at concentrations of 5-40%, 40-80%, 5-25%, 25-50%, 50-80%, 5-15%, 15-25%, 25-35%, 35-45%, 45%-55%, 65-75% or 75-80% by weight of the polymer.

For pH and $CO_2$ triggerable gels the practical monomers include vinyl pyridine, 2-(dimethylamino)ethyl acrylate, 2-(diethylamino)ethyl acrylate, 3-(dimethylamino)propyl acrylate or similar acrylic and pyridine based monomers, and/or acrylic acid. Embodiments including acrylic acid could produce a pH triggerable gel which would swell with high pH and shrink with low pH. Embodiments of temperature triggerable gels practical monomers include N-isopropylacrylamide. For ionic concentration triggerable gels, embodiments of the practical monomers include vinylimidazole or substituted versions thereof. For example, you could have 18-crown-6 substituted monmers to swell with potassium, or 15-crown-5 for sodium, etc. Practical monomers can be included in the smart gel polymer at 5-80% by weight of the smart gel polymer. For example, the practical monomer can be added at concentrations of 5-40%, 40-80%, 5-25%, 25-50%, 50-80%, 5-15%, 15-25%, 25-35%, 35-45%, 45%-55%, 65-75% or 75-80% by weight of the smart gel polymer.

To form the smart gel the copolymers can be cross-linked with a di-functional monomer such as ethylene glycol dimethacyrlate, methylene bis-acrylamide, triethyleneglycol trimethacyrlate, divinyl- or trivinyl benzene, or other multi-functional monomers. The copolymers may be cross-linked at a low level, such as with a concentration of cross-linker of less than 1%, to produce a lightly cross-linked gel with the ability to expand in volume significantly by taking up water, for example. The cross-linker can be included in the polymer of the smart gel in concentrations of less than 2%, less than 1.5%, less than 1%, less than 0.9%, less than 0.8%, less than 0.7%, less than 0.6%, less than 0.5%, less than 0.4%, less than 0.3%, less than 0.2%, and less than 0.1% of the polymer. For example, the concentrations of cross-linker can be 0.01-1.5%, 0.5-1.5%, 0.01-1%, 0.01-0.5%, 0.5%-1%, 0.01-0.3%, 0.3%-0.6%, 0.6%-1%, 0.01-0.1%, 0.1-0.2%, 0.2-0.3%, 0.3-0.4%, 0.4-0.5%, 0.5-0.6%, 0.6-0.7%, 0.7-0.8%, 0.8-0.9%, 0.9-1% by weight of the polymer.

In embodiments of the disclosure, the polymer of the smart gel is prepared by emulsion polymerization and the particle size can be controlled by surfactant and co-surfactant choice as well as monomer concentration. Variation of the monomer ratios in the initial reaction mixture results in smart gels that contain corresponding amounts of pH sensitive monomer in the back bone of the polymers and can be used to control the amount of swelling the smart gel undergoes. The reaction results in an emulsion which can be used as produced if desired or the microspheres can be separated by centrifugation and washed to eliminate the surfactants and any unreacted monomers. Suspensions of the separated microspheres can be prepared to the desired concentration in the injection/working fluid. The suspension compositions can be tailored to contain a narrow particle size or a broad range of particle size distribution based on the application.

In embodiments of the disclosure, the smart gel is comprised within a working fluid. Previous percentages listed in relation to the concentrations of monomers and cross-linkers within the polymer of the smart gel are exclusive of the concentration of working fluid. In embodiments, the working fluid may be water, brine, and/or a drilling fluid. The smart gel may comprise between 1-50% by weight of the working fluid. For example, the smart gel may comprise 1-25 wt %, 25-50 wt %, 1-10 wt %, 11-20 wt %, 21-30 wt %, 31-40 wt %, 41-50 wt % of the working fluid. The working fluid may be formulated to better distribute the smart gel into voids meant to be sealed by the smart gel. The trigger may also be comprised within a working fluid such as water or brine.

In embodiments of the disclosure, the smart gel is injected into voids in a well where they reside until they experience a trigger. The trigger may be externally applied, such as through a fluid injection, or can be an internal trigger, such as temperature change within the formation. One type of void is a microannulus. The microannulus can occur in a wellhead, in cement, in casing, or in tubing, for example. The trigger can be pH, $CO_2$, temperature, ionic strength, and so forth. The smart gel can experience the trigger when a trigger fluid is pumped into the voids where the smart gel resides. For example, if the trigger is high to low pH, the smart gel would reside in a fluid that has a higher pH, and the trigger fluid would have a lower pH. Further, the trigger can also be present in the well prior to injection of the smart gel into the well. That is, the trigger could be sourced into the well prior to injection of the smart gel or the trigger could be native to the well. For example, $CO_2$ can decrease the pH of fluids it is exposed to. If $CO_2$ comes in contact with a smart gel in a void, the $CO_2$ can then cause a high to low pH change, triggering the smart gel to swell. A high to low or low to high pH triggered smart gel can be designed to be triggered at different pH. For example, the pH triggered smart gel can be triggered at between 5-8 pH, such as 5-6 pH, 6-7 pH, or 7-8 pH values. A specific embodiment of the disclosure is a high to low triggered reversible smart gel that swells to greater than 50× its original size when the pH drops from above 7 to the range between 6-7 pH, for example about 6.3. In a specific embodiment of this disclosure these pH-triggered reversible smart gels retain their swelling and collapsing properties at a temperature range from about 22° C. to no less than 70° C.

In embodiments of the disclosure, the trigger is temperature. For example, the trigger can be going from a high temperature to a lower temperature or a lower temperature to a higher temperature. In certain embodiments, the temperature trigger is between about 30 to 60° C. In other embodiments of the disclosure, the trigger is the concentration of certain ions. For example, the trigger could occur going from high to low concentration of ions in solution or from low to high concentration of ions in solution. For example, the smart gel could be comprised in water with low total dissolved solids and swells when it comes into contact with brine, or vice versa.

Smart gels can be tested to determine the conditions of swelling, for example, the pH range in which the gel swells, the amount of swelling and the particle size distribution, for example. Gels can be tested in a microfluidic flow assembly. Further testing can be done in microfluidic channels, such as microfluidic channels in glass or the channels 30 in cement seen in FIG. 3. A cement channel can be formed in a small cement block constructed of the same type of cement used in the well. The smart gel can then be injected into the cement channel, triggered, and measurements can be made to determine effectiveness of the gel seal. Measurements can include differential pressure, such that the strength of the plug formed by the smart gel is quantified. The gels can also be tested at different temperatures, in different materials, and under differing chemical conditions to determine the effects of these variables on gel performance. The smart gel may also include a fluorescent tag or visual dye to enhance visualization.

In addition to sealing voids or channels in the well-head, the smart gel may be used in other applications. For example, the smart gel can be used to seal void areas in a sand screen. When a sand screen is packed with sand, if not done properly, large void areas can occur. These sand screens with large void areas are not as efficient at screening out particles as properly packed sand screens. Without sealing, water, fluids, and oil can flow at a high velocity through the voids in the sand screen, which enhances erosion of the screen. In some instances, once the large voided areas within a sand screen are plugged by the smart gel, the swelling could be partially reversed by changing the trigger. That is, once the gel is swelled, a reverse trigger could be applied in a limited amount such that the gel only partially returns to its pre-swelled condition. In this way, some larger voids may still comprise a large amount of gel, but in the areas with smaller voids, the thin layer of gel would be removed such that the permeability of the sand pack is maintained while maintaining a gel plug in the void area.

In other embodiments, the smart gel is used to seal drilling induced voids in producing zones while drilling is occurring. Drilling a wellbore 20 through production zones can cause fracturing 23 to occur in the production zones 24 (FIG. 2a). These fractures 23 or voids can be in communication with the wellbore and, if not sealed, drilling mud and fluids can leak from the wellbore into the production zones clogging the zones. Sealing production zone voids with a smart gel would allow drilling fluids to still circulate up and down within the wellbore without allowing the drilling fluids to plug the production zone (FIG. 2b). After drilling is complete, the smart gel seals could be reversed and the voids cleaned, which would reestablish access to the production zones (FIG. 2c). In embodiments of the disclosure the smart gel size, surface properties, swelling, and crosslinking would be tailored to each application. In embodiments of the disclosure, the smart gel is reversible. That is, reversing the trigger event will cause the smart gel to shrink. For example, if going from above a 6.3 pH to below a 6.3 pH causes the smart gel to swell, going from below 6.3 pH to above 6.3 pH will cause the smart gel to shrink.

In other embodiments, the smart gel is used to seal well annuli in order to prevent migration of gas through and/or between the casing and cement, or cement and host rock. In embodiments, annular migration is indicated by sustained casing pressure in the annulus.

In some embodiments, the smart gel is used within a plugged and abandoned well. Some plugged and abandoned wells can be subject to a barrier failure, which, due to lack of accessibility are difficult to localize, access, and mitigate by standard techniques. In embodiments, the smart gel can be pumped into a porous zone through an adjacent well and triggered to seal both wells. In some embodiments, a pilot hole is drilled through the plugged well cement and the smart gel is pumped through the hole and triggered. In another embodiment, an image assisted small bore relief well is drilled in order to deliver the smart gel into a sealed well below the plug and then to trigger the smart gel.

In some embodiments, the smart gel is used to enhance top seal integrity of a reservoir near the wellbore (e.g., damaged by drilling and completion). For example, some reservoir top seals are damaged near the wellbore, which can limit injection operating pressures or rates. Sealants emplaced prior to injection can enhance the top seal or repair known breaches near the wellbore. In some embodiments, the smart gel is less dense than the liquid within the reservoir thereby allowing control of the sealant plume.

In embodiments of the disclosure, specific properties of the triggerable gels are considered when designing a gel for a certain application. The properties of the gels can be modified to fit certain applications which can include particle size prior to triggered swelling, surface properties such as polarity, hydrophobicity, charge prior to swelling, amount of swelling after being triggered, strength of the gel after swelling, and the type of trigger. For example, given a specific casing composition and assumed or measured microannulus size, the smart gel can be tailored to the microannulus and casing composition such that the smart gel enters the microannulus efficiently. In an embodiment, the average size of the smart gel prior to swelling can be less than the size of the microannulus, thus, assisting distribution within the microannulus. In embodiments of the disclosure, the average size of the smart gel microsphere is between 10 nanometers to 200 micrometers. In specific embodiments of the disclosure, the average size of the gel microspheres is 5-50, 50-100, 100-150, or 150-200 micrometers. In embodiments, the average size of the gel microspheres is 5-25, 25-50, 50-75, or 75-100 micrometers. In embodiments, the maximum average size of a microsphere is 100 micrometers. In embodiments, the smart gel is designed for a very narrow aperture of microannuli. In embodiments, the smart gels are used where conventional mitigation approaches (e.g., cement squeezes, commercial sealants) would be ineffective.

As indicated above, in embodiments of the disclosure the average gel particle size is tailored to a specific application. For example, the smart gel is tailored to the size regime of the voids, such as cracks and/or pores in the reservoir, so that one can manipulate a synthetic variable to control the size and distribution of the smart gel polymer so that optimal flow of the suspension into the voids can be achieved. Embodiments include conducting experiments using a microfluidic cell and microscopic visualization and image analysis system to quantify the relationships among microannulus aperture distribution, particle size distribution and particle surface properties. For example, the particle size distribution of gel particles is a consideration in that the particles can be sufficiently small to flow through the microannulus network and yet be sufficiently large enough to seal the microannulus upon swelling. Flow through experiments using a custom microfluidic cell with engineered channels has shown flow characteristics of specific gel particles. Gel particles used in the experiment were angular, blocky and ranged from equidimensional to aspect ratios typically less than 2:1 (longest dimension:shortest dimension). In embodiments of the disclosure, the gel particle size may be designed to be 0.05-0.25 times the width of the microannulus network, as shown in the flow through experiments. For example, if the microannulus is 100 micrometers, the size of the gel particles can be 5 micrometers to 25 micrometers. Similar calculations can be done for other types of voids.

In one embodiment of the disclosure, smart gel sealant activation trigger design is application specific. In certain example embodiments, $CO_2$ can be used as the gel trigger. In other example embodiments, a $CO_2$ seal-sensitive trigger design can be controlled by pH. Smart gel triggers can be designed to activate via external stimuli such as through a trigger that is pumped into the well. The trigger may also be an internal trigger from the well, such as the presence of $CO_2$, an internal temperature change, or the like. The gels expand upon sensing the $CO_2$ or pH trigger and collapse on the removal of the trigger. The gel trigger may also be reversible, for example, the gel viscosity can increase or decrease upon responding to the trigger. Additionally, triggering could be through exposure to molecular $CO_2$ (no water), carbonic acid (CO2 dissolving in water to reduce pH) or simply acidity (e.g., souring that commonly occurs in water floods).

In embodiments of the disclosure, the smart gel is used to seal voids that are in contact with or near the wellbore region. The voids may be fractures, microannulus, voids in a sand screen, cracks, or the like. The area near the wellbore region could be a region that is within 20 meters of the wellbore, within 10 meters of the wellbore, within 7 meters of the wellbore, within 5 meters of the wellbore, within 3 meters of the wellbore, within 2 meters of the wellbore, within 1 meter of the wellbore, or within 0.5 meters of the wellbore.

Example embodiments allow for more efficient sealing of void areas within a well. Using example embodiments can provide significant cost savings, a higher level of reliability, easier installation, and easier maintenance of wells.

EXAMPLE

Figure 4:
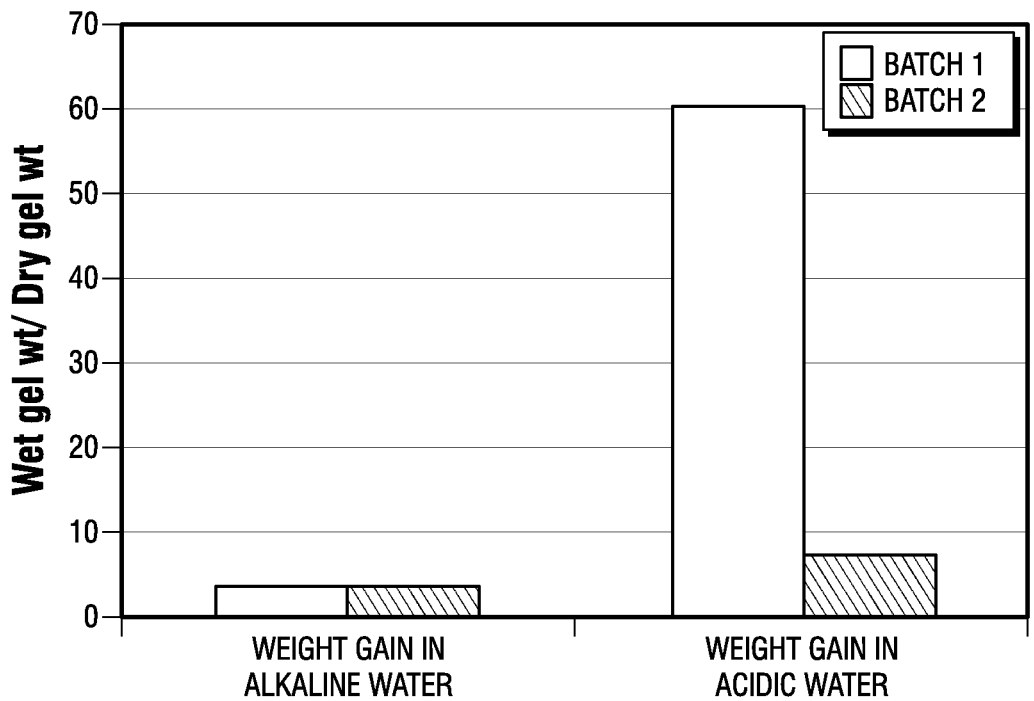
FIG. 4 shows the weight gain comparison of two smart gels in water with two different pHs.

Twelve different smart gel batches were synthesized and tested for swelling properties by carrying relative percentages of monomer and cross-linker with the trigger being pH. The particle size was controlled by the synthesis process. The smart gel example batches are given in the table below. Gels from batches 1 and 3 were shown to swell at pH values between 6 and 10 and 7 to 10 respectively. Weight gain after swelling for these two batches is shown in FIG. 4.

TABLE 2

Example compositions of a smart gel

| Monomer Ratio | Monomers | % fluorescent tag | % crosslinker |
|---|---|---|---|
| 1:1 | MMA:DMAEMA | 2 | 4 |
| 2:1 | MMA:DMAEMA | 0.2 | 7.6 |
| 1:3 | MMA:DMAEMA | 0.13 | 0.13 |
| 2:3 | MMA:DMAEMA | 0.1 | 2 |
| 1:1 | MMA:DMAEMA | 0.1 | 3.3 |
| 1:1 | MMA:2VP | 0.1 | 3.5 |
| 1:1 | MMA:2VP | 0.1 | 1 (DVB) |
| 1:1 | MMA:DMAEMA | 0.5 | 1 |
| 2:1 | MMA:DMAEMA | 0.5 | 1 |
| 1:2 | MMA:DMAEMA | 0.5 | 1 |
| 1:2 | MMA:2VP | 0.5 | 1 (DVB) |
| 2:1 | MMA:2VP | 0.5 | 1 (DVB) |

MA—Methyl methacrylate
MAEMA—2-(Dimethylamino) ethyl methacrylate
VP—2-Vinyl pyridine (alternative pH sensitive monomer)
NMA—2-Napthyl methacrylate (fluorescent tag)
GDMA—Ethylene glycol dimethacrylate (crosslinker)
VB—Divinylbenzene (alternative crosslinker)

Figure 5:
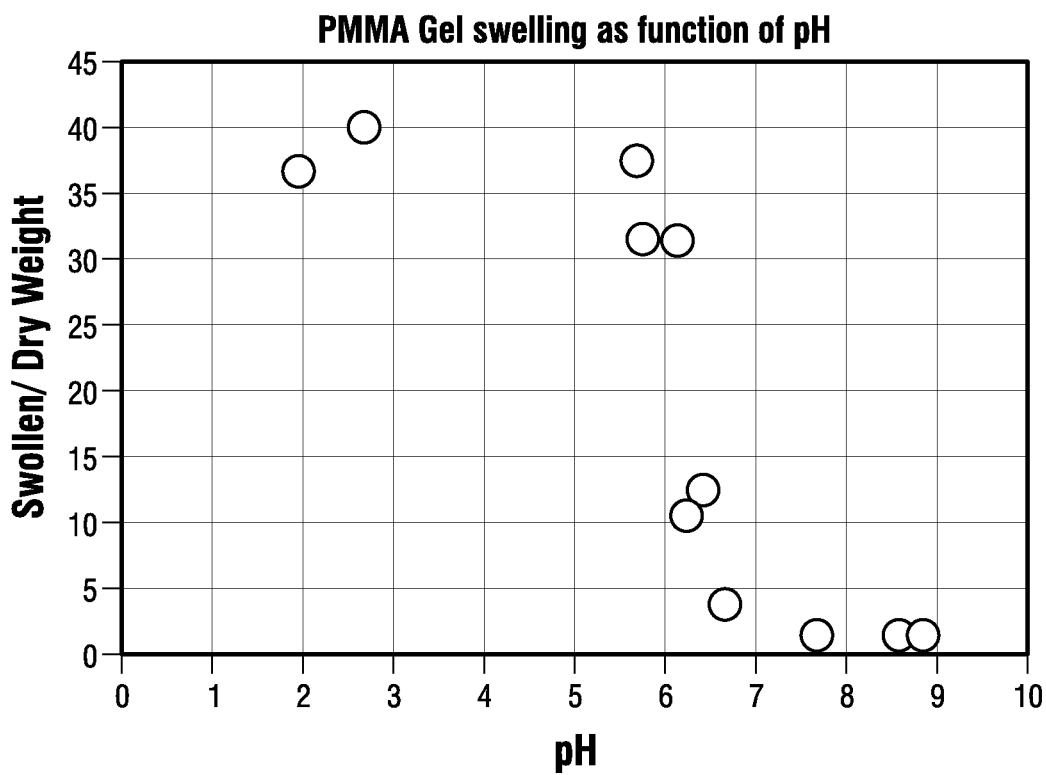
FIG. 5 illustrates a smart gel swelling as a function of pH.
Figure 6:
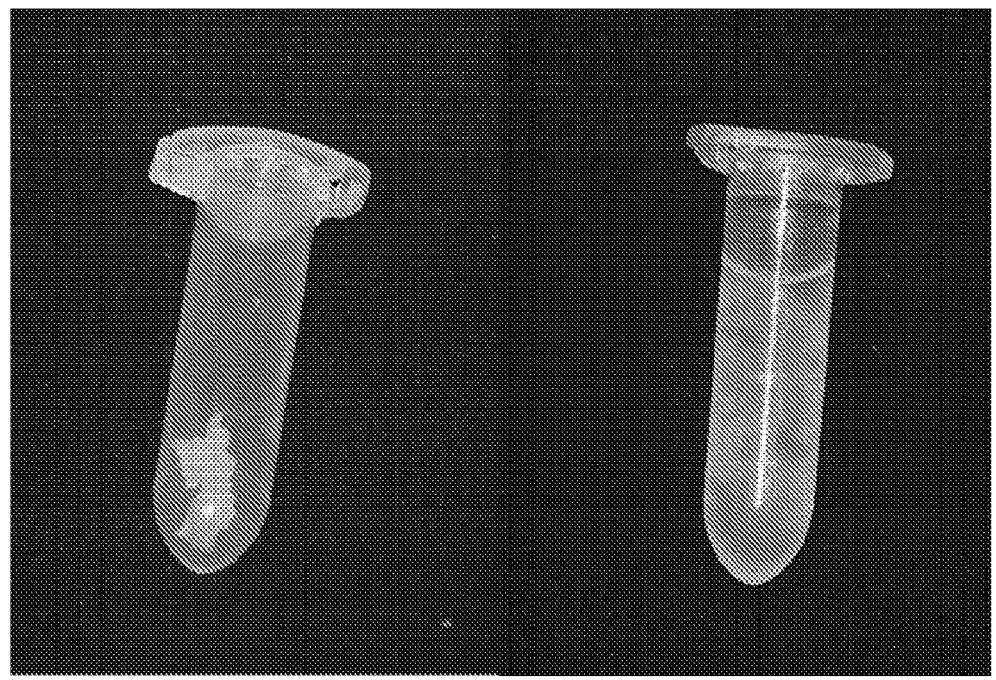
FIG. 6 is a photograph of the unswollen gel (left) and the swollen gel (right).
Figure 7:
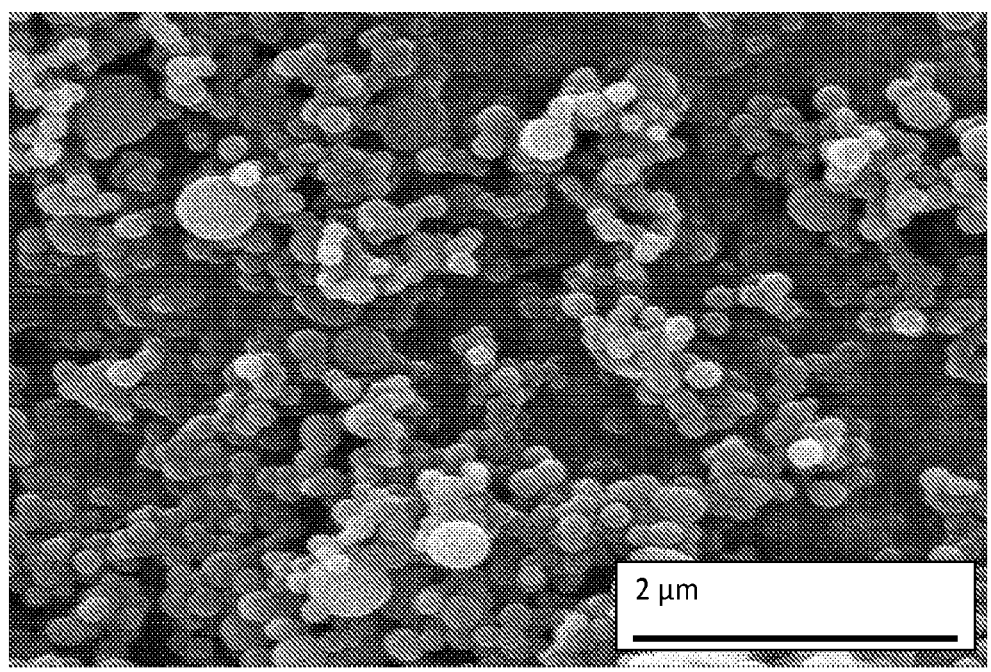
FIG. 7 is a scanning electron microscope image of gel particles.

Three additional gel batches beyond those above have been characterized including testing variable swelling properties as a function of pH. One such test is shown in FIG. 5, where a gel swelled up to 40 times its dry weight at pH below 6. Smart gel swelling and the reversible effect of collapsing were shown to be consistent in a temperature range from about 22° C. to 70° C. Particle size varied from 100 nm to 800 micrometers when collapsed. Particle size distributions were relatively narrow, and additional distributions could be achieved through mixing. FIG. 6 is a photograph of an unswollen gel on the left and the swollen gel on the right. Each vial is approximately 3 cm tall. FIG. 7 is a scanning electron microscope of the gel particles.

Figure 3:
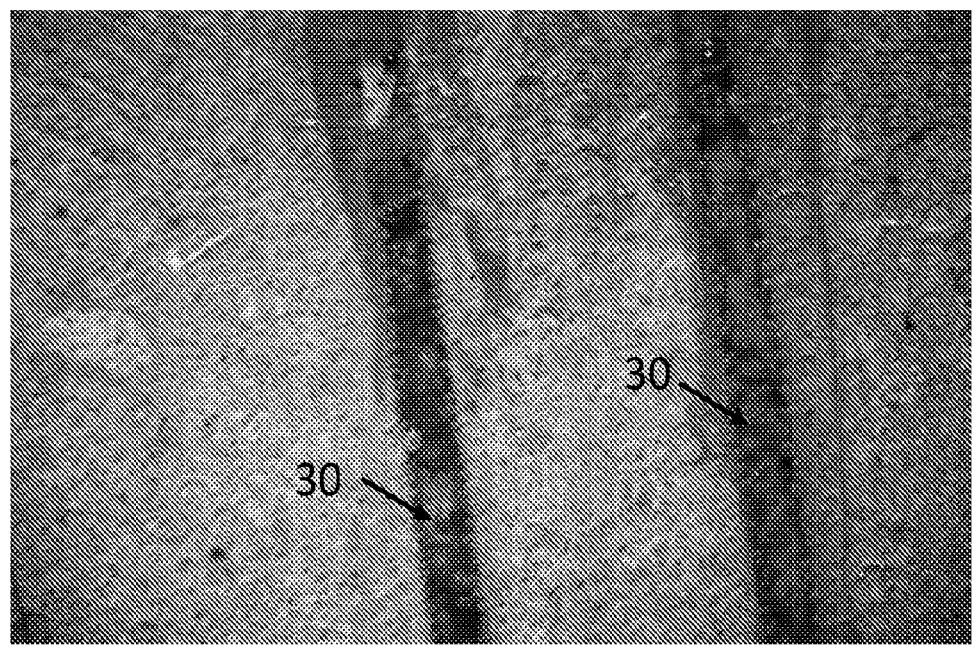
FIG. 3 is a photograph of two about 400 mm wide voids carved in cement. Both voids are clogged with smart gel in response to a pH change. The sealant is stained showing up dark gray. The dark gray can be seen both within the central voids and extend out into smaller fractures.

Several gel batches were tested in fabricated cement and glass micromodels with laser-etched microannulus and natural microannulus. The void thickness in the cement micromodels ranged from 100 micrometers to 3000 micrometers. Good visualization was achieved. FIG. 3 shows an photograph of a gel that was injected in its collapsed state into a cement micromodel comprising two voids 30 and then caused to swell by lowering the pH. The sealant was originally stained red, but shows up as a uniform dark gray in the figure. The dark gray can be seen plugging both the central voids 30 and also plugging smaller fractures which extend out into the cement. For example, the dark gray line that runs from top to bottom to the right of the right void 30 is plugged with swollen gel particles. Swollen particles also plug the top of the left most void 30 and extend into fractures in the cement on the right and left at the top of the void 30. The swollen gel particles effectively plugged the channel and prevented fluid flow.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

REFERENCES

All references listed here are incorporated herein by reference in full.

Bourgoyne, et al., 1999 Bourgoyne, Jr., Adam T., LSU; Scott, Stuart L., LSU; Manowski, Wojciech, Dowell-Schlumberger: "A Review of Sustained Casing Pressure (SCP) Occurring on the OCS", *LSU/MMS Well Control Workshop* (Apr. 1, 1998).

Goodman, H. E. 2012, "Taking control of subsurface behavior with Smart Gels—an oil & gas exploitation perspective, Goldschmidt Conference 2012, Montréal, Canada.

What is claimed is:

1. A method for sealing a void in a well comprising: injecting into the well a triggerable gel composition having an untriggered size and comprising a polymer, where the polymer comprises an inert monomer, a practical monomer, and less than 1.5% by weight of a cross-linker, wherein when the triggerable gel composition is exposed to CO2, the triggerable gel composition swells to at least ten times the untriggered size, wherein the triggerable gel composition does not comprise cement, and wherein the CO2 is present in the well prior to injecting the triggerable gel composition.

2. The method of claim 1, wherein the void being sealed is a void in a sand screen, a microannulus in a casing of the well, a void in a production zone of a well undergoing drilling, or a void in a plugged and abandoned well.

3. The method of claim 1, further comprising injecting the CO2 into the well that will trigger the gel composition to swell.

4. The method of claim 1, wherein the inert monomer is one or more of methyl methacrylate, styrene, alkyl substituted styrenes, methyl acrylate, methacrylic and acrylic monomers, acryloyl nitrile, polyvinylpyrolidinone and a substituted acrylamide.

5. The method of claim 1, wherein the inert monomer is 5-80% by weight of the triggerable gel.

6. The method of claim 1, wherein the practical monomer is one or more of 2-(dimethylamino) ethyl methacrylate, vinyl pyridine, 2-(diethylamino) ethyl acrylate, 3-(dimethylamino)propyl acrylate, and acrylic acid.

7. The method of claim 1, wherein the practical monomer is 5-80% by weight of the triggerable gel.

8. The method of claim 1, wherein the cross-linker is one or more of ethylene glycol dimethacrylate, methylene bis-acrylamide, triethyleneglycol trimethacyrlate, and divinyl- or trivinyl benzene.

9. The method of claim 1, wherein the triggerable gel composition is comprised within a working fluid.

10. The method of claim 1, wherein the void being sealed is within 1 meter of the well.

11. The method of claim 1, wherein the triggerable gel comprises gel particles with an average size between 10 nanometers and 100 micrometers prior to being triggered.

12. The method of claim 1, wherein the triggerable gel composition swells to at least fifty times the untriggered size when exposed to CO2.

13. A method comprising:
monitoring a well for a gas leak; and
upon detecting the gas leak, injecting into the well a triggerable gel composition having an untriggered size and comprising a polymer, where the polymer comprises an inert monomer, a practical monomer, and less than 1.5% by weight of a cross-linker, wherein when the triggerable gel composition is exposed to a trigger, the triggerable gel composition swells to at least ten times the untriggered size, and wherein the triggerable gel composition does not comprise cement.

14. The method of claim 13, further comprising injecting into the well a second composition comprising the trigger that will trigger the gel composition to swell.

15. The method of claim 13, wherein the trigger is a pH level, a temperature level, an ion concentration, magnetic waves, a pressure level, acoustic waves, electric waves or CO2.

16. The method of claim 13, wherein the trigger is CO2 and the CO2 is present in the well prior to injecting into the well the triggerable gel composition.

17. The method of claim 13, wherein the inert monomer is one or more of methyl methacrylate, styrene, alkyl substituted styrenes, methyl acrylate, methacrylic and acrylic monomers, acryloyl nitrile, polyvinylpyrolidinone and a substituted acrylamide.

18. The method of claim 13, wherein the inert monomer is 5-80% by weight of the triggerable gel.

19. The method of claim 13, wherein the practical monomer is one or more of 2-(dimethylamino) ethyl methacrylate, vinyl pyridine, 2-(diethylamino) ethyl acrylate, 3-(dimethylamino)propyl acrylate, and acrylic acid.

20. The method of claim 13, wherein the practical monomer is 5-80% by weight of the triggerable gel.

21. The method of claim 13, wherein the cross-linker is one or more of ethylene glycol dimethacrylate, methylene bis-acrylamide, triethyleneglycol trimethacyrlate, and divinyl- or trivinyl benzene.

22. The method of claim 13, wherein the triggerable gel composition is comprised within a working fluid.

23. The method of claim 13, wherein the triggerable gel comprises gel particles with an average size between 5 and 100 nanometers prior to being triggered.

24. The method of claim 13, wherein the triggerable gel composition swells to at least fifty times the untriggered size when exposed to CO2.

* * * * *